United States Patent
Yuan et al.

[11] Patent Number: 5,833,628
[45] Date of Patent: Nov. 10, 1998

[54] GRADUATED BONE GRAFT HARVESTER

[76] Inventors: Hansen Yuan, 5066 Pine Valley Dr., Fayatteville, N.Y. 13066; Peter Stutz, Obere Stadelstrasse 8, 3653 Oberhofrn, Switzerland; John Dowdle, 332 S. Mississippi River Blvd., St. Paul, Minn. 55105; Serafin Samson, 16929 Weaver Lake Dr., Maple Grove, Minn. 55311

[21] Appl. No.: 637,127
[22] Filed: Apr. 24, 1996
[51] Int. Cl.$^6$ .................................................. A61B 10/00
[52] U.S. Cl. ......................... 600/567; 606/180; 604/158
[58] Field of Search .................... 128/749–754, 128/760, 763, 771

[56] References Cited

U.S. PATENT DOCUMENTS

| | | |
|---|---|---|
| 2,526,662 | 10/1950 | Hipps et al. . |
| 2,542,828 | 2/1951 | Morrison . |
| 4,131,116 | 12/1978 | Hedrick . |
| 4,142,517 | 3/1979 | Stavropoulos et al. . |
| 4,447,235 | 5/1984 | Clarke .................................. 128/760 |
| 4,757,826 | 7/1988 | Abdulhay . |
| 4,777,947 | 10/1988 | Zwick . |
| 4,951,690 | 8/1990 | Baker . |
| 5,040,542 | 8/1991 | Gray . |
| 5,152,763 | 10/1992 | Johnson .................................. 606/86 |
| 5,269,785 | 12/1993 | Bonutti .................................. 606/80 |
| 5,301,684 | 4/1994 | Ogirala . |
| 5,335,672 | 8/1994 | Bennett . |
| 5,341,816 | 8/1994 | Allen . |
| 5,357,974 | 10/1994 | Baldridge . |
| 5,423,844 | 6/1995 | Miller . |
| 5,443,472 | 8/1995 | Li .......................................... 606/114 |
| 5,515,861 | 5/1996 | Smith .................................... 128/754 |
| 5,556,399 | 9/1996 | Huebner ................................ 606/80 |

FOREIGN PATENT DOCUMENTS

| | | |
|---|---|---|
| 0 317 503 | 5/1989 | European Pat. Off. . |
| 2 233 972 | 1/1975 | France . |
| 87 01582 | 8/1988 | France . |
| 29 27 160 | 7/1979 | Germany . |
| 1602487 A1 | 10/1990 | U.S.S.R. . |
| 1669434 A1 | 8/1991 | U.S.S.R. . |

*Primary Examiner*—Max Hindenburg
*Assistant Examiner*—Pamela L. Wingood
*Attorney, Agent, or Firm*—Vidas, Arrett & Steinkraus

[57] ABSTRACT

A disposable, bone graft harvester having a clear, graduated plastic tube tipped with a bone cutting head at one end and a handle or other torque supplying connection at the other end.

2 Claims, 6 Drawing Sheets

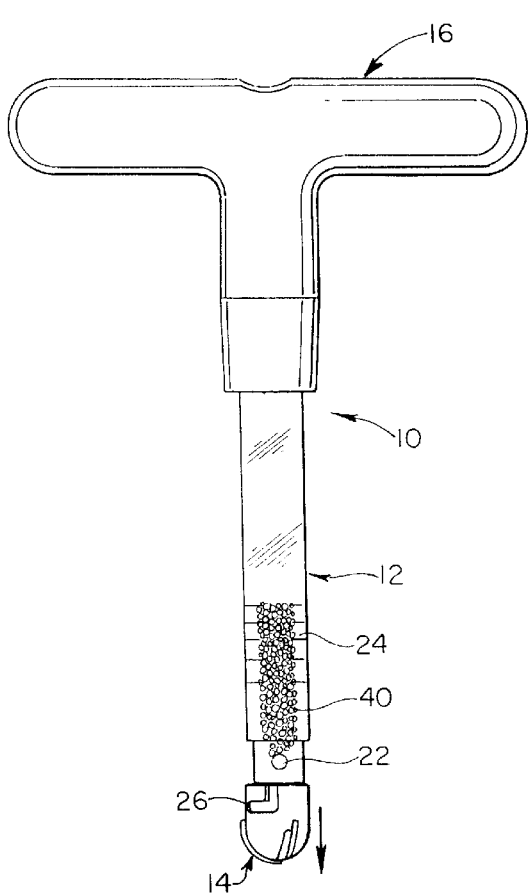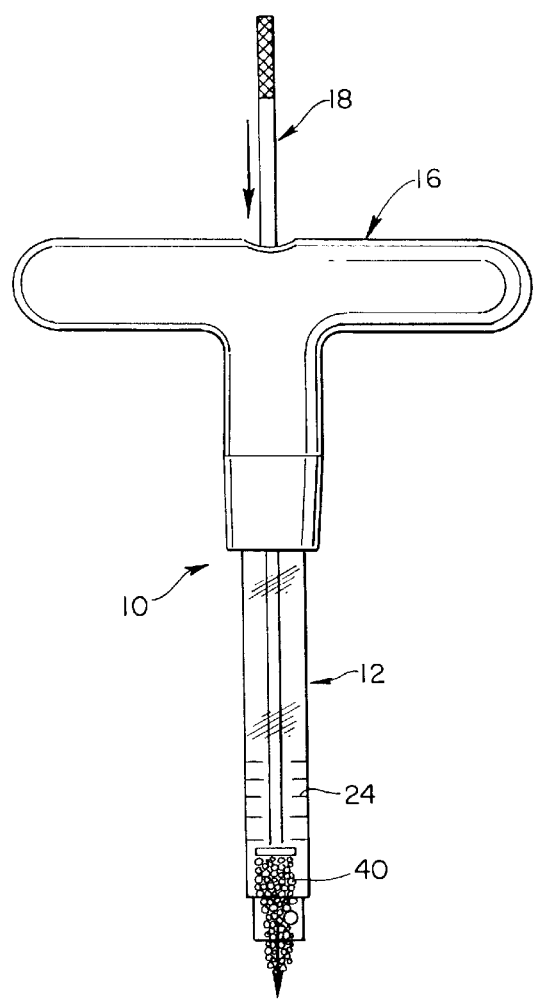

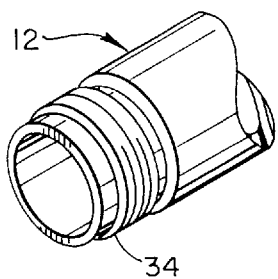
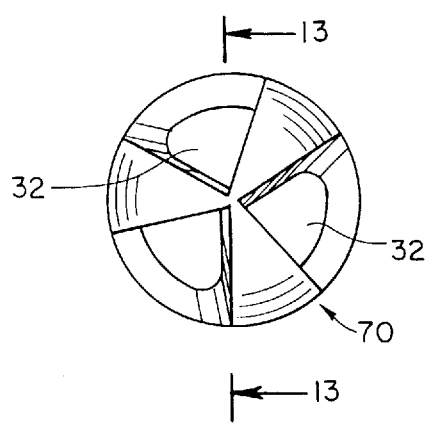
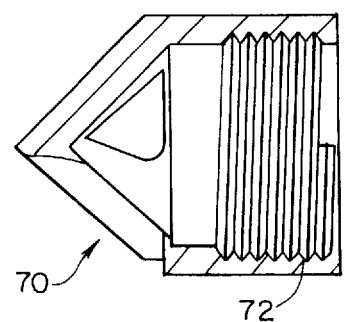

GRADUATED BONE GRAFT HARVESTER

BACKGROUND OF THE INVENTION

1. Field of the Invention

This invention relates to a device for harvesting bone graft.

2. Description of the Related Art

Bone graft is utilized in many surgical procedures. It is often harvested from bone from the hip. Often, a simple chisel approach has been employed to dig out bone which often results in a wound site that is more painful than the site in which the harvested bone is to be used.

U.S. Pat. No. 5,341,816 issued to Allen shows a biopsy device including a long, solid shaft 24 having a T-handle at one end and a hollow cavity at the other end to receive a cartridge assembly of a clear plastic tube and a steel cutter. The harvested tissue is seen in the plastic tube through a slots in the shaft's hollow cavity. After collection, the cartridge assembly is unscrewed and the tissue is ejected by a push rod inserted through the open end of the cutter.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

The invention provides a unique bone harvester in which the physician may quickly obtain the volume of bone required with minimal invasiveness. It employs a disposable harvester having a clear plastic tubular body which has gradations along its length to readily show the volume of material harvested by a single glance. One end of the clear plastic tube is tipped by a cutting head and the other end includes a handle or other torque supplying connection. The device is simply rotated into the bone, causing bone to be milled by the cutting head and pulled into the barrel of the clear tube. The gradations on the tube allow the physician to immediately know the volume harvested.

BRIEF DESCRIPTION OF THE DRAWINGS

A detailed description of the invention is hereafter described with specific reference being made to the drawings in which:

FIG. 4 is a side elevational view illustrating removal of the drill head to retrieve harvested bone;

FIG. 5 is a side elevational view showing the drill head removed and plunging out the harvested bone;

FIG. 11 shows the device of FIG. 1 with a threaded distal tube end;

FIG. 12 shows an alternate cutting head; and

FIG. 13 shows a cross-section of the cutting head of FIG. 12 taken along lines 13—13.

DESCRIPTION OF THE PREFERRED EMBODIMENTS

Figure 1:
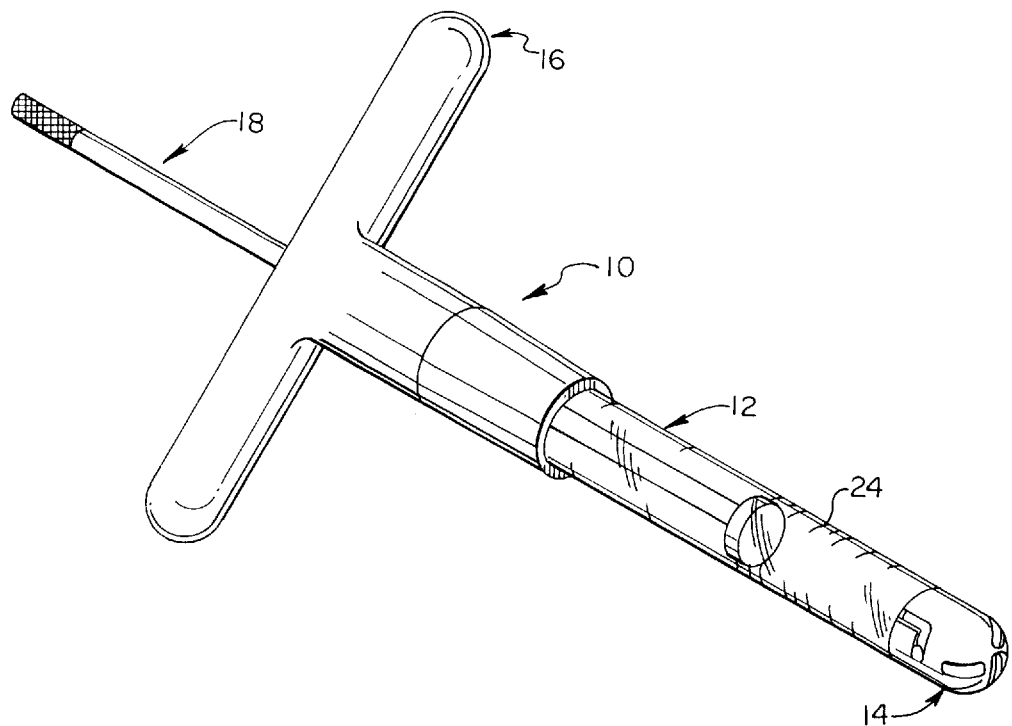
FIG. 1 is a perspective view of the invention.
Figure 2:
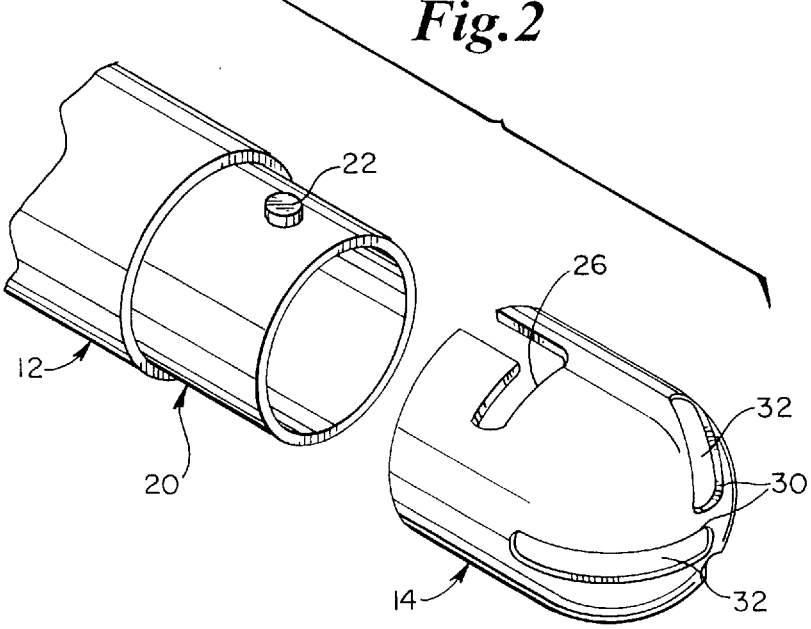
FIG. 2 is an exploded perspective view showing the drill head.

The main components of the bone harvester device 10 of the invention are shown in FIG. 1 and include the clear, graduated plastic tube 12, a cutting head 14, a T-handle 16 and a bone extractor plunger 18. As shown in FIG. 2, the attachment between the cutting head 14 and the tube 12 may be by a formed end 20 with lock buttons 22 which engage with an L-slot 26 in the cutting head. The cutting head 14 has a number of cutting edges 30 formed along the cutting slots 32. The number and arrangement of the slots 32 and cutting edges 30 may be varied depending on the size of the harvested bone pieces desired.

Figure 3:
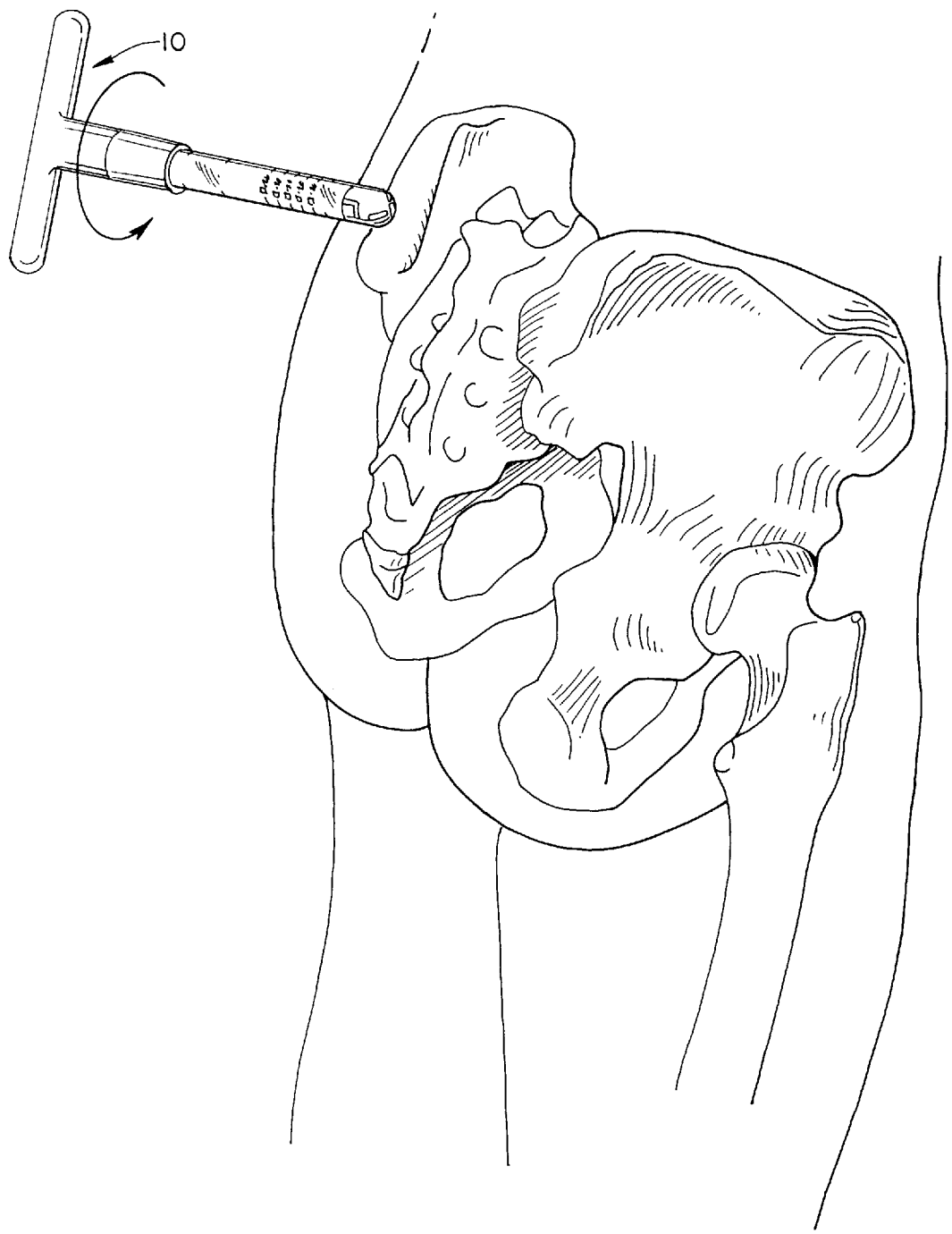
FIG. 3 is a perspective view demonstrating the harvesting of bone from a hip.
Figure 6:
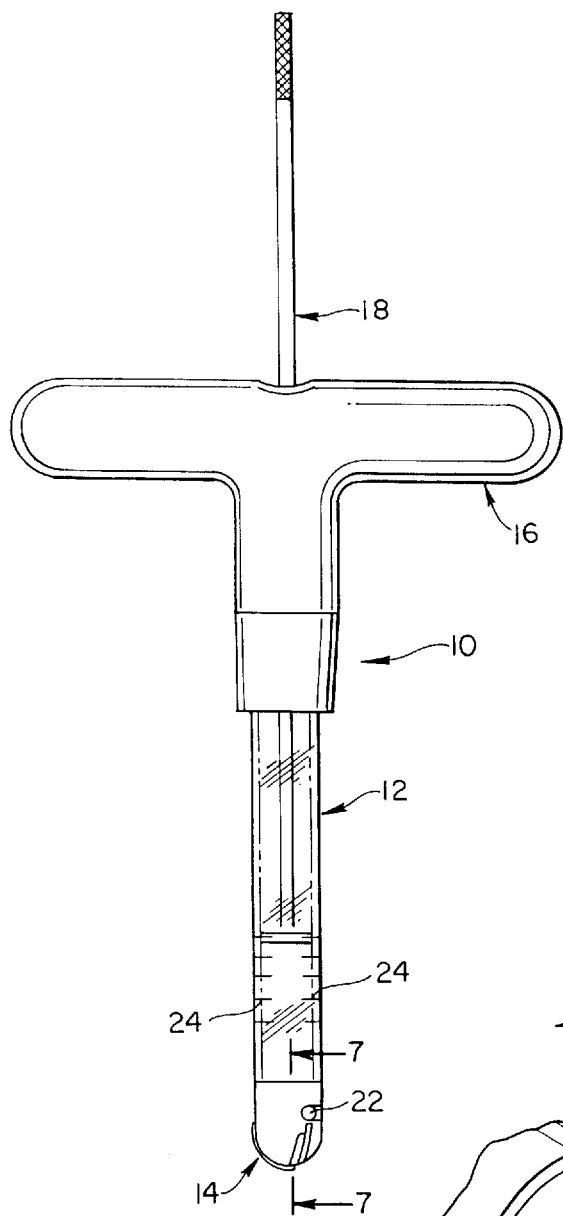
FIG. 6 is a side elevational view illustrating the drill head assembled.
Figure 7:
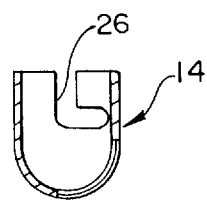
FIG. 7 is a cross-sectional view taken from line 7—7 in FIG. 6.

A number of gradation marks 24 may be etched or otherwise placed on the plastic tube 12 to show volume of bone harvested. When the surgeon is harvesting bone from the iliac crest 74 as depicted in FIG. 3, the site is exposed via a small incision and a starter trocar may be used to penetrate the outer bone. The device 10 of the invention is then positioned as shown and gently rotated against the bone, causing the cutting edges 30 to create small bone chips which enter the hollow tube via the slots 32. As the tool 10 is used, the harvested bone 40 fills up the clear tube 12, passing each of the gradations 24 until the desired volume is reached. At that point, the tool is withdrawn and the cutting head 14 is removed. A bone extractor plunger 18 is then inserted through the hollow T-handle 16 to eject the harvested bone 40 from the device so it may be used as desired.

Figure 8:
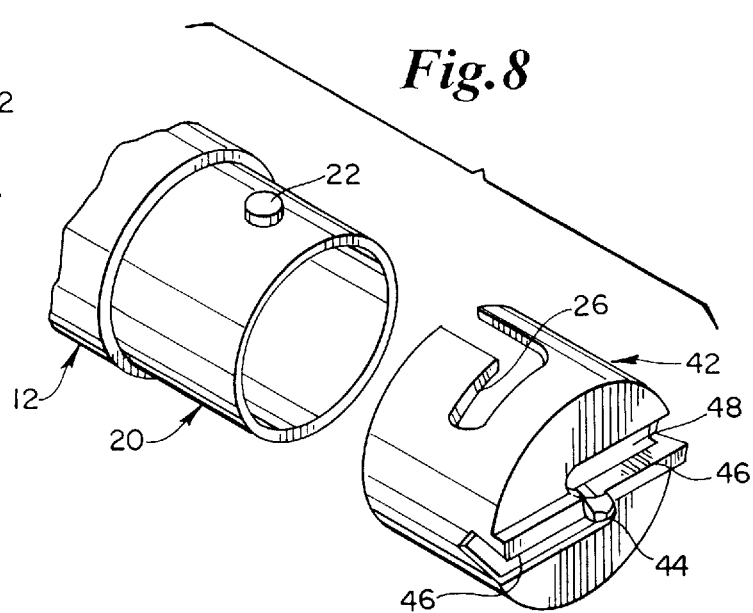
FIG. 8 is an exploded perspective view showing an alternate cutting head.

The cutting head 14 includes cutting edges 30 and slots 32 to carve chips of bone which enter the hollow tube 12. The slot and edge combination sizes the bone chips and prevents the bone from exiting the hollow tube 12 when withdrawn from the harvest site. In FIG. 8, an alternate cutting head 42 is shown in which a centrally located spike 44 is located between two cutting edges 46 and slots 48. It should be recognized that angles of the cutting edges and size of the slots may be varied to select different sized bone chips. A conical cutting head 70 is shown in FIGS. 12 and 13, along with threads 72 to mate to a threaded tube 12 as in FIG. 11. Also, the attachment to the hollow tube 12 via lock buttons 22 and L-slots 26 are simply one of many means to attach the cutting head 14 to the tube 12. FIG. 11 shows that attachment may be by a threaded end 34.

Figure 9:
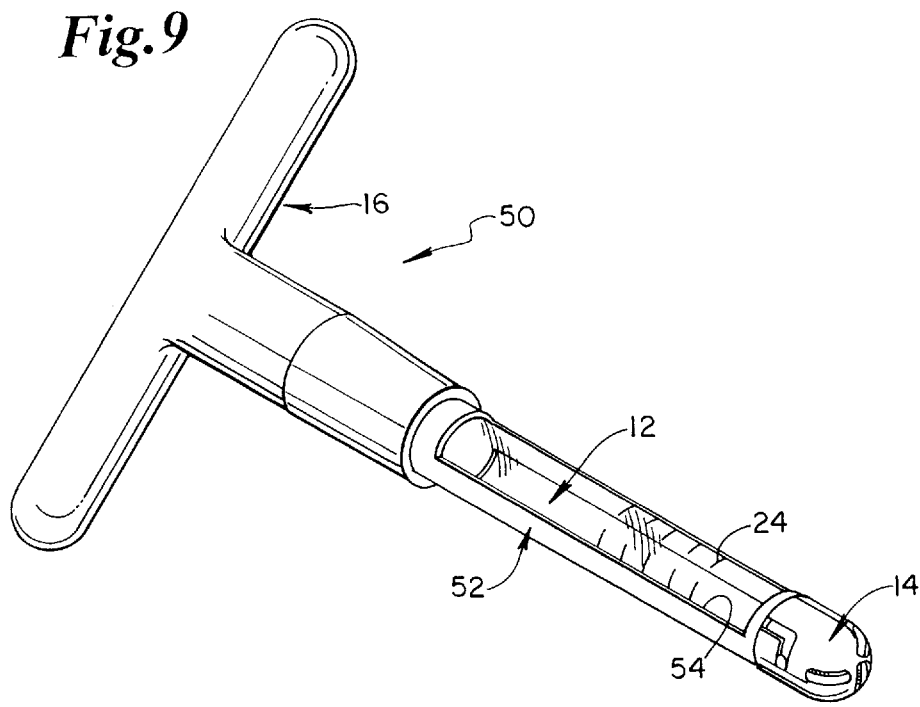
FIG. 9 is a perspective view of an alternative embodiment of the invention.
Figure 10:
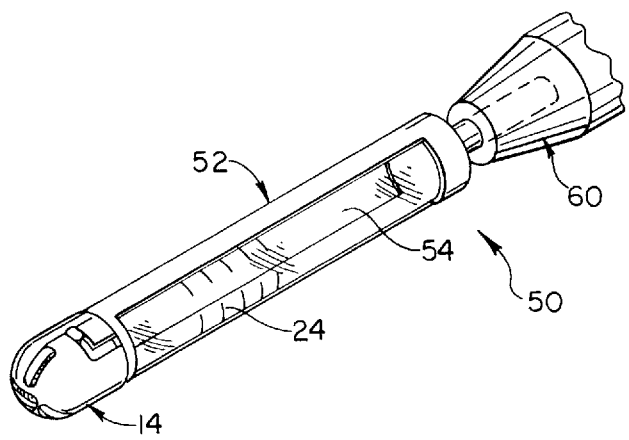
FIG. 10 shows the device of FIG. 9 attached to a power take-off connection.

In the device 50 of the invention shown in FIGS. 9 and 10, the device is strengthened by a reinforcing framework 52 that surrounds the hollow tube 12. In this embodiment, the framework would typically be formed of stainless steel and would provide the connection to the cutting head at the distal end and to the T-handle or power take-off at the proximal end. As shown, the framework 52 would leave at least two longitudinal slots 54 extending substantially the entire length of the clear tube 12 so the harvested bone could be seen. The device 50 of FIGS. 9 and 10 would have greater strength and may be able to harvest bone without the need for a starter trocar. The intimate arrangement of the clear tube 12 against the reinforcing framework 52 increases the torque that may be applied to the cutting head without damage to the device 50. The tube may be formed by a combination of clear plastic and the metal framework such that clear plastic is inset into windows in the metal framework.

Gradations 24 may be placed on the clear tube 12, the framework 52 or both, to show volume of harvested bone 40. FIG. 10 shows the device attached to a power drill 60. Any power take-off connection may be used to attach the proximal end to a rotary drill, including Hudson fittings and the like.

In the device shown in FIGS. 9 and 10, the method of use is similar to that previously described, although a starting trocar may not be needed. In all cases, the cutting head is removed after the bone is harvested and bone is extracted by pushing it out of the clear tube 12 from the proximal to the distal end.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

| S56.2–5798 GRADUATED BONE GRAFT HARVESTER REFERENCE NUMERAL LIST | |
|---|---|
| # | |
| 10 | device |
| 12 | clear, graduated plastic tube |
| 14 | cutting head |
| 16 | T-handle |
| 18 | bone extractor plunger |
| 20 | formed end, clear tube |
| 22 | lock buttons |
| 24 | gradations |
| 26 | L-slot on end 20 |
| 30 | cutting edges |
| 32 | cutting slots |
| 34 | threaded end |
| 36 | |
| 38 | |
| 40 | harvested bone |
| 42 | cutting head |
| 44 | spike |
| 46 | cutting edge |
| 48 | slot |
| 50 | reinforced device |
| 52 | reinforced framework |
| 54 | longitudinal slots |
| 56 | |
| 58 | |
| 60 | drill |
| 62 | |
| 64 | |
| 66 | |
| 68 | |
| 70 | Conical cutting head |
| 72 | threads (cutter FIG. 13) |
| 74 | iliac crest |
| 76 | |
| 78 | |
| 80 | |

What is claimed is:

1. A bone graft harvester comprising:
   a) an elongated transparent hollow tube having a proximal and a distal end;
   b) reinforced framework secured about said hollow tube, said framework extending from the proximal to the distal end of said hollow tube, said framework being constructed and arranged to define at least two longitudinal slots through which said hollow tube may be seen along substantially the entire length of said hollow tube;
   c) a bone cutting head attached in fluid communication to the reinforced framework at the distal end of said tube, said bone cutting head being constructed such that when torque is applied to said bone cutting head, said bone cutting head will rotate into contacted bone resulting in the harvesting of distinct and separate bone chips which enter said hollow tube, said cutting head being constructed and arranged to prevent said bone chips from exiting said cutting head when removed from a harvesting site, said bone cutting head being removable;
   d) an attachment connected to said reinforced framework at the proximal end of the tube which allows torque to be supplied to the device, said attachment having an opening in communication with said tube to allow a plunger to pass proximally into said hollow tube to eject harvested bone distally after removal of said bone cutting head;
   e) said bone graft harvester including a plurality of gradation marks on said reinforced framework, said hollow tube or both to represent volume markers for said hollow tube.

2. A bone graft harvester comprising:
   a) an elongated transparent hollow tube having a proximal and a distal end;
   b) a reinforced framework having a proximal and a distal end, said framework being constructed and arranged to define at least two longitudinal slots, each of said longitudinal slots being closed by an inset transparent plastic, said framework and inset plastic defining a hollow tube, said slots and inset plastic providing a view of the interior of said hollow tube along substantially the entire length of said hollow tube;
   c) a bone cutting head attached in fluid communication to the reinforced framework at the distal end of said framework, said bone cutting head being constructed such that when torque is applied to said bone cutting head, said bone cutting head will rotate into contacted bone resulting in the harvesting of distinct and separate bone chips which enter said hollow tube, said cutting head being constructed and arranged to prevent said bone chips from exiting said cutting head when removed from a harvesting site, said bone cutting head being removable;
   d) an attachment connected to said reinforced framework at the proximal end of the tube which allows torque to be supplied to the device, said attachment having an opening in communication with said tube to allow a plunger to pass proximally into said hollow tube to eject harvested bone distally after removal of said bone cutting head; and
   e) said bone graft harvester including a plurality of gradation marks on said reinforced framework, said plastic insets or both to represent volume markers for said hollow tube.

* * * * *